(12) United States Patent
Yamanaka et al.

(10) Patent No.: US 9,005,976 B2
(45) Date of Patent: Apr. 14, 2015

(54) SELECTION METHOD OF INDUCED PLURIPOTENT STEM CELLS

(75) Inventors: Shinya Yamanaka, Kyoto (JP); Takayuki Tanaka, Kyoto (JP)

(73) Assignee: Kyoto University, Kyoto (JP)

( * ) Notice: Subject to any disclaimer, the term of this patent is extended or adjusted under 35 U.S.C. 154(b) by 185 days.

(21) Appl. No.: 13/393,528

(22) PCT Filed: Sep. 1, 2010

(86) PCT No.: PCT/JP2010/065357
§ 371 (c)(1),
(2), (4) Date: Feb. 29, 2012

(87) PCT Pub. No.: WO2011/027901
PCT Pub. Date: Mar. 10, 2011

(65) Prior Publication Data
US 2012/0156684 A1    Jun. 21, 2012

Related U.S. Application Data

(60) Provisional application No. 61/238,800, filed on Sep. 1, 2009.

(51) Int. Cl.
*C12N 15/00* (2006.01)
*C12Q 1/68* (2006.01)

(52) U.S. Cl.
CPC ........ *C12Q 1/6881* (2013.01); *C12Q 2600/158* (2013.01)

(58) Field of Classification Search
USPC .................................................. 435/455, 325
IPC ...................................................... C12N 5/0696
See application file for complete search history.

(56) References Cited

U.S. PATENT DOCUMENTS

2010/0184051 A1    7/2010 Hochedlinger

FOREIGN PATENT DOCUMENTS

WO    WO 2008/151058 A2    12/2008

OTHER PUBLICATIONS

Takahashi (Cell, 2006, vol. 126:663-676).*
Takahashi (Cell, 2007, vol. 131: 861-872).*
Maherali (Cell Stem Cell, Jul. 2007, vol. 1, p. 55-70).*
Yu (Science, 2007, vol. 318, p. 1917-1920).*
Blelloch (Cell Stem Cell, Sep. 13, 2007, vol. 1, p. 245-247).*
Nakagawa (Nat Biotechnol, Jan. 2008, vol. 26: 101-106; published online Nov. 11, 2007).*
Aoi (Science, Aug. 2008, vol. 321, p. 699-702; published online Feb. 14, 2008).*
Okita (Science, Nov. 7, 2008, vol. 322, p. 949-953).*
Kim (Cell, Feb. 6, 2009, vol. 136, p. 411-419).*
Feng (Cell Stem Cell, Apr. 3, 2009, vol. 4, p. 301-312).*
Loh (Blood, May 28, 2009, vol. 113, No. 22, p. 5476-5479).*
Gonzalez (PNAS, Jun. 2, 2009, vol. 106, No. 22, p. 8918-8922).*
Hotta (J. Cell. Biochem., Sep. 2008, vol. 105, p. 940-948).*
Papapetrou (PNAS, Aug. 4, 2009, vol. 106, No. 31, p. 12759-12764).*
Yamanaka (Nature, Jul. 2, 2009, vol. 460, No. 7251, p. 49-52).*
Applied Biosystems manual in 6 pages (2006).
Chan, E.M., et al., Live Cell Imaging Distinguishes Bona Fide Human iPS Cells From Partially Reprogrammed Cells, Nat. Biotechnol. 27(11):1033-1037, 2009.
Hotta, A., et al., Retroviral Silencing in iPS Cell Induction, J. Cell Biochem. 105(4):940-948, 2008.
Papapetrou, E.P., et al., Stoichiometric and Temporal Requirements of Oct4, Sox2, Klf4, and c-Myc Expression for Efficient Human iPSC Induction and Differentiation, Proc. Natl. Acad. Sci. USA 106(31):1259-12764, 2009.
Varas, F., et al., Fibroblast-Derived Induced Pluripotent Stem Cells Show No Common Retroviral Vector Insertions, Stem Cells 27(2):300-306, 2009.
Yamanaka, S., Elite and Stochastic Models for Induced Pluripotent Stem Cell Generation, Nature, 460(7251):49-52, 2009.

* cited by examiner

*Primary Examiner* — Michael Wilson
(74) *Attorney, Agent, or Firm* — Knobbe, Martens, Olson & Bear LLP

(57) ABSTRACT

The present invention relates to a method for selecting induced pluripotent stem (iPS) cells. More particularly, the present invention provides: a method for selecting an iPS cell, comprising the steps of: (1a) measuring the expression level of an exogenous nuclear reprogramming gene(s) in a test iPS cell; and (2a) selecting an iPS cell in which the expression level(s) of an exogenous nuclear reprogramming gene(s) is/are less than or equal to the expression level(s) in control iPS cells; and a method for selecting an iPS cell, comprising the steps of: (1b) measuring the expression level of an exogenous nuclear reprogramming gene(s) and the sum the expression levels of the exogenous nuclear reprogramming gene(s) and the corresponding endogenous gene iPS cell; and (2b) selecting an iPS cell in which the ratio of the expression level of an exogenous nuclear reprogramming gene(s) relative to the sum of the expression levels of the exogenous transgene(s) and the corresponding endogenous gene(s) is less than 1 to the ratio in the control iPS cell.

6 Claims, 4 Drawing Sheets

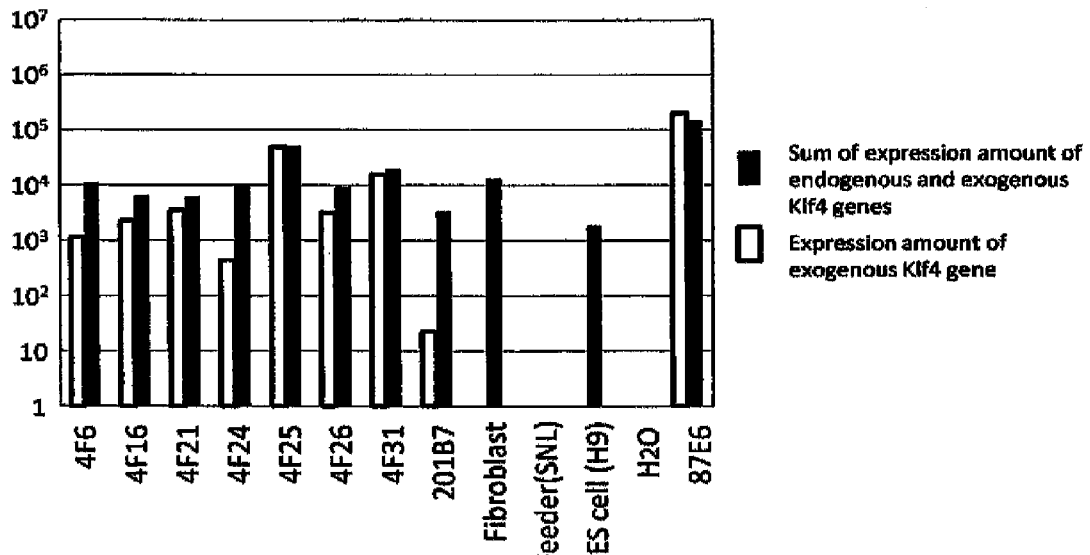
Fig. 3 Klf4
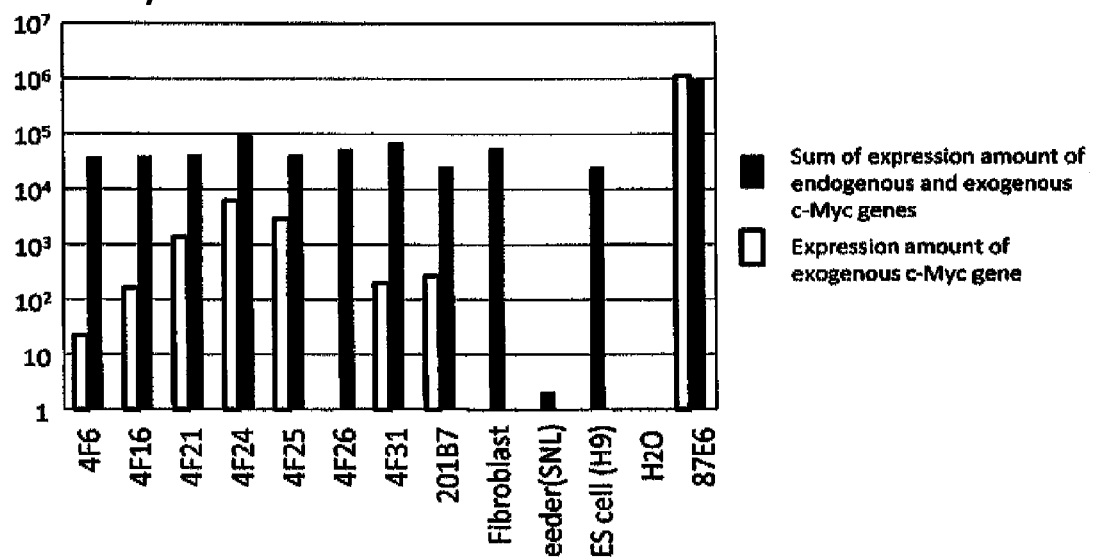
Fig. 4 c-Myc

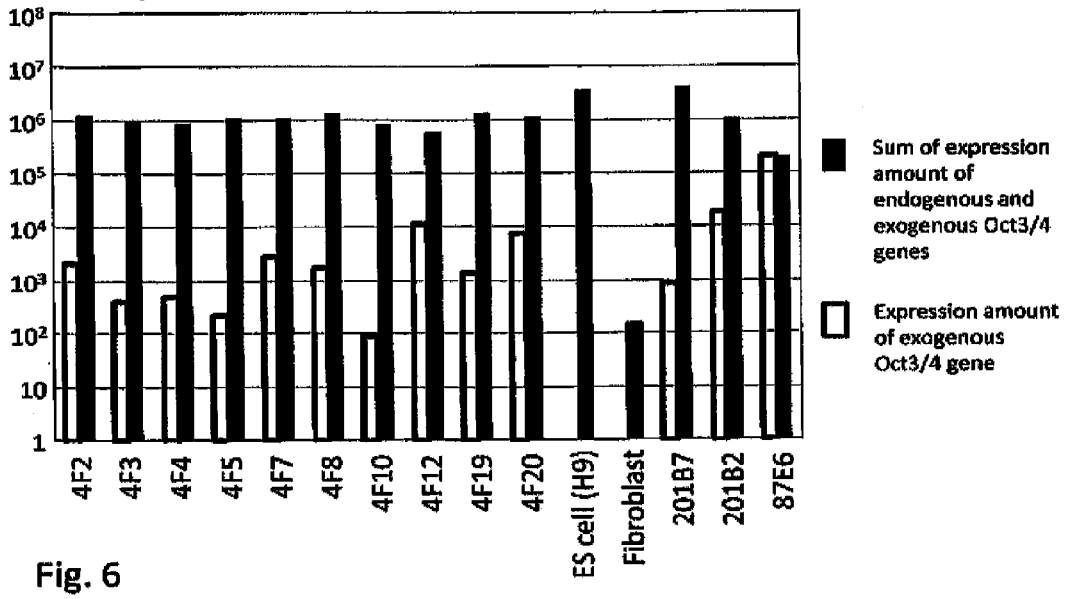
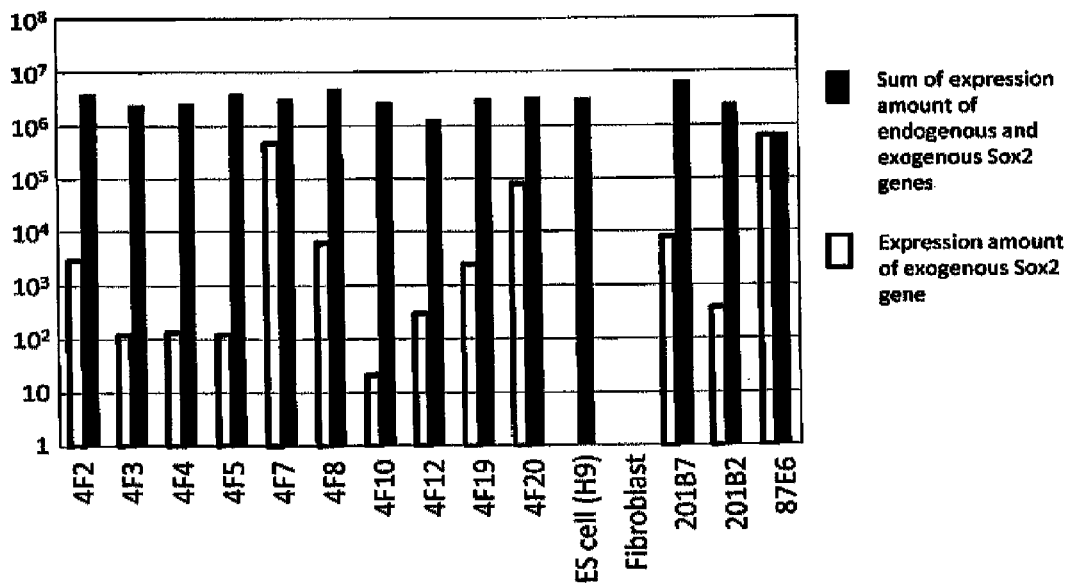

```
                           SEQUENCE LISTING

<160> NUMBER OF SEQ ID NOS: 19

<210> SEQ ID NO 1
<211> LENGTH: 23
<212> TYPE: DNA
<213> ORGANISM: Artificial sequence
<220> FEATURE:
<223> OTHER INFORMATION: sense primer for OCT3/4(total)

<400> SEQUENCE: 1
ccccagggcc ccattttggt acc                                          23

<210> SEQ ID NO 2
<211> LENGTH: 26
<212> TYPE: DNA
<213> ORGANISM: Artificial sequence
<220> FEATURE:
<223> OTHER INFORMATION: antisense primer for OCT3/4(total)

<400> SEQUENCE: 2
acctcagttt gaatgcatgg gagagc                                       26

<210> SEQ ID NO 3
<211> LENGTH: 24
<212> TYPE: DNA
<213> ORGANISM: Artificial sequence
<220> FEATURE:
<223> OTHER INFORMATION: sense primer for SOX2(total)

<400> SEQUENCE: 3
ttcacatgtc ccagcactac caga                                         24

<210> SEQ ID NO 4
<211> LENGTH: 26
<212> TYPE: DNA
<213> ORGANISM: Artificial sequence
<220> FEATURE:
<223> OTHER INFORMATION: antisense primer for SOX2(total)

<400> SEQUENCE: 4
tcacatgtgt gagaggggca gtgtgc                                       26

<210> SEQ ID NO 5
<211> LENGTH: 30
<212> TYPE: DNA
<213> ORGANISM: Artificial sequence
```

```
<220> FEATURE:
<223> OTHER INFORMATION: sense primer for Klf4(total)

<400> SEQUENCE: 5
gattacgcgg gctgcggcaa aacctacaca                                              30

<210> SEQ ID NO 6
<211> LENGTH: 30
<212> TYPE: DNA
<213> ORGANISM: Artificial sequence
<220> FEATURE:
<223> OTHER INFORMATION: antisense primer for Klf4(total)

<400> SEQUENCE: 6
ttaaaaatgt ctcttcatgt gtaaggcgag                                              30

<210> SEQ ID NO 7
<211> LENGTH: 24
<212> TYPE: DNA
<213> ORGANISM: Artificial sequence
<220> FEATURE:
<223> OTHER INFORMATION: sense primer for c-Myc(total)

<400> SEQUENCE: 7
atacatcctg tccgtccaag caga                                                    24

<210> SEQ ID NO 8
<211> LENGTH: 30
<212> TYPE: DNA
<213> ORGANISM: Artificial sequence
<220> FEATURE:
<223> OTHER INFORMATION: antisense primer for c-Myc(total)

<400> SEQUENCE: 8
tcacgcacaa gagttccgta gctgttcaag                                              30

<210> SEQ ID NO 9
<211> LENGTH: 23
<212> TYPE: DNA
<213> ORGANISM: Artificial sequence
<220> FEATURE:
<223> OTHER INFORMATION: sense primer for OCT3/4(transgene)

<400> SEQUENCE: 9
gctctcccat gcattcaaac tga                                                     23

<210> SEQ ID NO 10
<211> LENGTH: 23
<212> TYPE: DNA
<213> ORGANISM: Artificial sequence
<220> FEATURE:
<223> OTHER INFORMATION: antisense primer for OCT3/4(transgene)

<400> SEQUENCE: 10
cttacgcgaa atacgggcag aca                                                     23

<210> SEQ ID NO 11
<211> LENGTH: 24
<212> TYPE: DNA
<213> ORGANISM: Artificial sequence
<220> FEATURE:
<223> OTHER INFORMATION: sense primer for SOX2(transgene)

<400> SEQUENCE: 11
ttcacatgtc ccagcactac caga                                                    24
```

```
<210> SEQ ID NO 12
<211> LENGTH: 24
<212> TYPE: DNA
<213> ORGANISM: Artificial sequence
<220> FEATURE:
<223> OTHER INFORMATION: antisense primer for SOX2(transgene)

<400> SEQUENCE: 12
gacatggcct gcccggttat tatt                                          24

<210> SEQ ID NO 13
<211> LENGTH: 23
<212> TYPE: DNA
<213> ORGANISM: Artificial sequence
<220> FEATURE:
<223> OTHER INFORMATION: sense primer for Klf4(transgene)

<400> SEQUENCE: 13
ccacctcgcc ttacacatga aga                                           23

<210> SEQ ID NO 14
<211> LENGTH: 24
<212> TYPE: DNA
<213> ORGANISM: Artificial sequence
<220> FEATURE:
<223> OTHER INFORMATION: antisense primer for Klf4(transgene)

<400> SEQUENCE: 14
gacatggcct gcccggttat tatt                                          24

<210> SEQ ID NO 15
<211> LENGTH: 24
<212> TYPE: DNA
<213> ORGANISM: Artificial sequence
<220> FEATURE:
<223> OTHER INFORMATION: sense primer for c-Myc(transgene)

<400> SEQUENCE: 15
atacatcctg tccgtccaag caga                                          24

<210> SEQ ID NO 16
<211> LENGTH: 24
<212> TYPE: DNA
<213> ORGANISM: Artificial sequence
<220> FEATURE:
<223> OTHER INFORMATION: antisense primer for c-Myc(transgene)

<400> SEQUENCE: 16
gacatggcct gcccggttat tatt                                          24

<210> SEQ ID NO 17
<211> LENGTH: 30
<212> TYPE: DNA
<213> ORGANISM: Artificial sequence
<220> FEATURE:
<223> OTHER INFORMATION: sense primer for Klf4(total)

<400> SEQUENCE: 17
catgccagag gagcccaagc caaagagggg                                    30

<210> SEQ ID NO 18
<211> LENGTH: 30
<212> TYPE: DNA
<213> ORGANISM: Artificial sequence
<220> FEATURE:
<223> OTHER INFORMATION: antisense primer for Klf4(total)
```

```
<400> SEQUENCE: 18
cgcaggtgtg ccttgagatg ggaactcttt                              30

<210> SEQ ID NO 19
<211> LENGTH: 22
<212> TYPE: DNA
<213> ORGANISM: Artificial sequence
<220> FEATURE:
<223> OTHER INFORMATION: antisense primer for c-Myc(total)

<400> SEQUENCE: 19
acgcacaaga gttccgtagc tg                                      22
```

SELECTION METHOD OF INDUCED PLURIPOTENT STEM CELLS

REFERENCE TO SEQUENCE LISTING

The present application is filed along with a Sequence Listing in electronic format. The Sequence Listing is provided as a file entitled SEQLIST-TOYA166013APC.TXT, created Feb. 29, 2012, which is approximately 4.0 KB in size. The information in the electronic format of the Sequence Listing is incorporated herein by reference in its entirety.

TECHNICAL FIELD

The present invention relates to a method for selecting an induced pluripotent stem (hereinafter referred to as iPS) cell which is highly safe for clinical application. More particularly, the present invention relates to:
a method for selecting an iPS cell, comprising the steps of:
(1a) measuring the expression level of an exogenous nuclear reprogramming gene(s) in a test iPS cell; and (2a) selecting an iPS cell in which the expression level(s) of an exogenous nuclear reprogramming gene(s) is/are less than or equal to the expression level(s) in the control iPS cell.
The present invention also relates to:
a method for selecting an iPS cell, comprising the steps of:
(1b) measuring the expression level of an exogenous nuclear reprogramming gene(s) and sum of the expression levels of the exogenous nuclear reprogramming gene(s) and the corresponding endogenous gene(s) in a test iPS cell; and (2b) selecting an iPS cell in which the ratio of the expression level of the exogenous nuclear reprogramming gene(s) relative to the sum of the expression levels of the exogenous nuclear reprogramming gene(s) and the corresponding endogenous gene(s) is less than or equal to the ratio in the control iPS cell.
The present invention also relates to primer sets for PCR for measuring the sum of the expression levels of the exogenous nuclear reprogramming gene(s) and the corresponding endogenous gene(s), and primer sets for PCR for measuring only the expression level of the exogenous nuclear reprogramming gene(s).

BACKGROUND ART

In recent years, iPS cells of mouse and human have been established. Yamanaka et al. established iPS cells by introduction of Oct3/4, Sox2, Klf4 and c-Myc genes into mouse-derived fibroblasts and their forced expression therein (1, 2). Thereafter, it was found that iPS cells can be prepared with 3 factors, without the c-Myc gene (3). Further, Yamanaka et al. succeeded in establishment of iPS cells by introduction of 4 human genes which correspond to the mouse genes into skin-derived fibroblasts of human (1, 4). On the other hand, Thomson et al. prepared human iPS cells by using Nanog and Lin28 instead of Klf4 and c-Myc (5, 6).

Virus vectors such as retroviruses and lentiviruses are excellent vectors in view of their higher gene transfer efficiencies as compared with non-viral vectors, which enable simple preparation of iPS cells using them. However, retroviruses and lentiviruses are incorporated into chromosomes. Similarly, even with a plasmid vector which is generally considered to be less prone to be incorporated into chromosomes, a stably expressing cell line in which the reprogramming genes are incorporated into chromosomes is obtained at a certain frequency, which may be due to requirement of continuous high expression of the reprogramming factors in establishment of the iPS cells (7, 8).

On the other hand, after establishment of iPS cells, there are cases where repression of expression (or silencing) of the incorporated exogenous genes occurs. Such iPS cells in which expression of the incorporated exogenous genes is repressed are preferably used for clinical application, and so on.

Thus, a method for assaying whether expression of exogenous transgenes is repressed and a method for selecting an iPS cell by assessing the gene repression are demanded.

REFERENCES

1. WO 2007/069666 A1
2. Takahashi, K. and Yamanaka, S., *Cell*, 126: 663-676 (2006)
3. Nakagawa, M. et al., *Nat. Biotechnol.*, 26: 101-106 (2008)
4. Takahashi, K. et al., *Cell*, 131: 861-872 (2007)
5. WO 2008/118820 A2
6. Yu, J. et al., *Science*, 318: 1917-1920 (2007)
7. Okita, K. et al., *Science*, 322: 949-953 (2008)
8. Kaji, K. et al., *Nature*, 458: 771-775 (2009)

SUMMARY OF THE INVENTION

The present invention aims to efficiently select an iPS cell (iPS cell clone) which is safe and suitable for clinical application. Therefore, the present invention provides a method for selecting an iPS cell (iPS cell clone), especially human iPS cell, in which expression of a transgene(s) is repressed, and to provide a method for production of a safe iPS cell using the above method.

In order to solve the above objects, the present inventors first used quantitative PCR to measure the expression level of the exogenous transgenes (nuclear reprogramming genes) and sum of the expression levels of the exogenous transgenes and the corresponding endogenous genes in human iPS cell lines 201B2 and 201B7, where silencing of the transgenes was determined by comparing the cells right after transfection (Takahashi, K. et al., *Cell*, 131: 861-872 (2007)). As a result, it was found that the expression level of the exogenous transgenes was low and that the ratio of the expression level of the exogenous transgenes relative to the sum of the expression levels of the exogenous transgenes and the corresponding endogenous genes was low. On the other hand, it was confirmed that, in iPS cells in which expression of the exogenous genes was not repressed, the ratio of the expression level of the exogenous transgenes relative to the sum of the expression levels of the exogenous transgenes and the corresponding endogenous gene was high.

From the results above, the present inventors discovered that iPS cells in which expression of the exogenous transgenes is repressed can be selected based on the expression level of the exogenous transgenes or the ratio of the expression level of the exogenous transgenes relative to the sum of the expression levels of the exogenous transgenes and the corresponding endogenous genes, thereby completed the present invention.

An aspect of the present invention is to provide a method for selecting, from induced pluripotent stem cells (population of iPS cell clones) established by introduction of an exogenous nuclear reprogramming gene(s) to somatic cells, an induced pluripotent stem cell (iPS cell clone) in which expression of the exogenous nuclear reprogramming gene(s) is repressed, said method comprising the steps of:
(a) measuring the expression level of said exogenous nuclear reprogramming gene(s) in a test induced pluripotent stem cell; and (b) selecting an induced pluripotent stem cell in which the expression level of the exogenous nuclear reprogramming gene(s) is less than or equal to a control value(s).

Another aspect of the present invention is to provide the method as described above, wherein said nuclear reprogramming gene(s) to be measured comprise(s) at least one selected from the group consisting of Oct3/4, Sox2, Klf4 and c-Myc.

Another aspect of the present invention is to provide the method as described above, wherein said nuclear reprogramming genes to be measured comprise at least two selected from the group consisting of Oct3/4, Sox2, Klf4 and c-Myc.

Another aspect of the present invention is to provide the method as described above, wherein said nuclear reprogramming genes to be measured comprise at least three selected from the group consisting of Oct3/4, Sox2, Klf4 and c-Myc.

Another aspect of the present invention is to provide the method as described above, wherein said nuclear reprogramming genes to be measured are Oct3/4, Sox2, Klf4 and c-Myc.

Another aspect of the present invention is to provide the method as described above, wherein said control value is less than or equal to 10000 copies per 50 ng of total RNA in the induced pluripotent stem cell.

Another aspect of the present invention is to provide the method as described above, wherein said control value is less than or equal to 1000 copies per 50 ng of total RNA in the induced pluripotent stem cell.

Another aspect of the present invention is to provide the method as described above, wherein
(i) said control value for Oct3/4 is 18700 copies per 50 ng of total RNA in the induced pluripotent stem cell;
(ii) said control value for Sox2 is 7950 copies per 50 ng of total RNA in the induced pluripotent stem cell;
(iii) said control value for Klf4 is 2990 copies per 50 ng of total RNA in the induced pluripotent stem cell; and
(iv) said control value for c-Myc is 4020 copies per 50 ng of total RNA in the induced pluripotent stem cell.

Another aspect of the present invention is to provide the method as described above, wherein said control values are the expression levels of said nuclear reprogramming genes in 201B7 cell and/or 201B2 cell.

Another aspect of the present invention is to provide a method for selecting, from induced pluripotent stem cells (population of iPS cell clones) established by introduction of an exogenous nuclear reprogramming gene(s) to somatic cells, an induced pluripotent stem cell (iPS cell clone) in which expression of the exogenous nuclear reprogramming gene(s) is repressed, said method comprising the following steps of:

(a) measuring the expression level of the exogenous nuclear reprogramming gene(s) and the sum of the expression levels of the exogenous nuclear reprogramming gene(s) and the corresponding endogenous gene(s) in a test induced pluripotent stem cell; and (b) selecting an induced pluripotent stem cell in which the ratio of the expression level of the exogenous nuclear reprogramming gene(s) relative to the sum of the expression levels of the exogenous nuclear reprogramming gene(s) and the corresponding endogenous gene(s) is less than or equal to a control ratio.

Another aspect of the present invention is to provide the method as described above, wherein said nuclear reprogramming gene(s) to be measured comprise(s) at least one selected from the group consisting of Oct3/4, Sox2, Klf4 and c-Myc.

Another aspect of the present invention is to provide the method as described above, wherein said nuclear reprogramming genes to be measured comprise at least two selected from the group consisting of Oct3/4, Sox2, Klf4 and c-Myc.

Another aspect of the present invention is to provide the method as described above, wherein said nuclear reprogramming genes to be measured comprise at least three selected from the group consisting of Oct3/4, Sox2, Klf4 and c-Myc.

Another aspect of the present invention is to provide the method as described above, wherein said nuclear reprogramming genes to be measured are Oct3/4, Sox2, Klf4 and c-Myc.

Another aspect of the present invention is to provide the method as described above, wherein said control ratio is less than or equal to 5%.

Another aspect of the present invention is to provide the method as described above, wherein said control ratio is less than or equal to 2%.

Another aspect of the present invention is to provide the method as described above, wherein:
(i) said control ratio for Oct3/4 is 1.8%;
(ii) said control ratio for Sox2 is 0.16%;
(iii) said control ratio for KlfF4 is 10.4%; and
(iv) said control ratio for c-Myc is 4.7%.

Another aspect of the present invention is to provide the method as described above, wherein said control ratio is the ratio of the expression level of the exogenous nuclear reprogramming gene(s) relative to the sum of the expression levels of the exogenous nuclear reprogramming gene(s) and the corresponding endogenous gene(s) in 201B7 cell and/or 201B2 cell.

Another aspect of the present invention is to provide the method as described above, wherein the expression level of said exogenous nuclear reprogramming gene(s) is measured using a primer set described in Table 3.

Another aspect of the present invention is to provide the method as described above, wherein the expression level of said exogenous nuclear reprogramming gene(s) and the sum of the expression levels of the exogenous nuclear reprogramming gene(s) and the corresponding endogenous gene(s) are measured using primer sets described in Table 3.

Another aspect of the present invention is to provide any one of the primer sets for PCR described in Table 3.

Another aspect of the present invention is to provide a kit for selecting an induced pluripotent stem cell, comprising any one of the primer sets for PCR described in Table 3.

According to the present invention, iPS cells in which expression of the transgene(s) is repressed can be selected. Thus, the present invention is very useful in the application of human iPS cells established by using a retrovirus or the like as a regenerative medicine.

BRIEF DESCRIPTION OF THE DRAWINGS

FIG. 3 shows the results of measurement of the expression level of the mRNA of Klf4.

FIG. 4 shows the results of measurement of the expression level of the mRNA of c-Myc.

FIG. 5 shows the results of measurement of the expression level of the mRNA of Oct3/4.

FIG. 6 shows the results of measurement of the expression level of the mRNA of Sox2.

Figure 1:
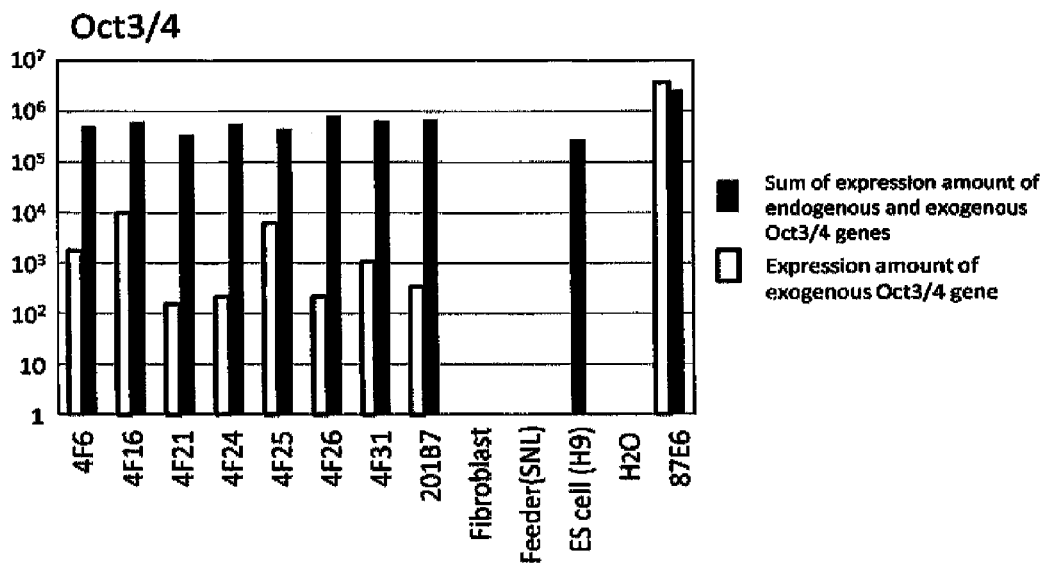
FIG. 1 shows the results of measurement of the expression level of the mRNA of Oct3/4.
Figure 2:
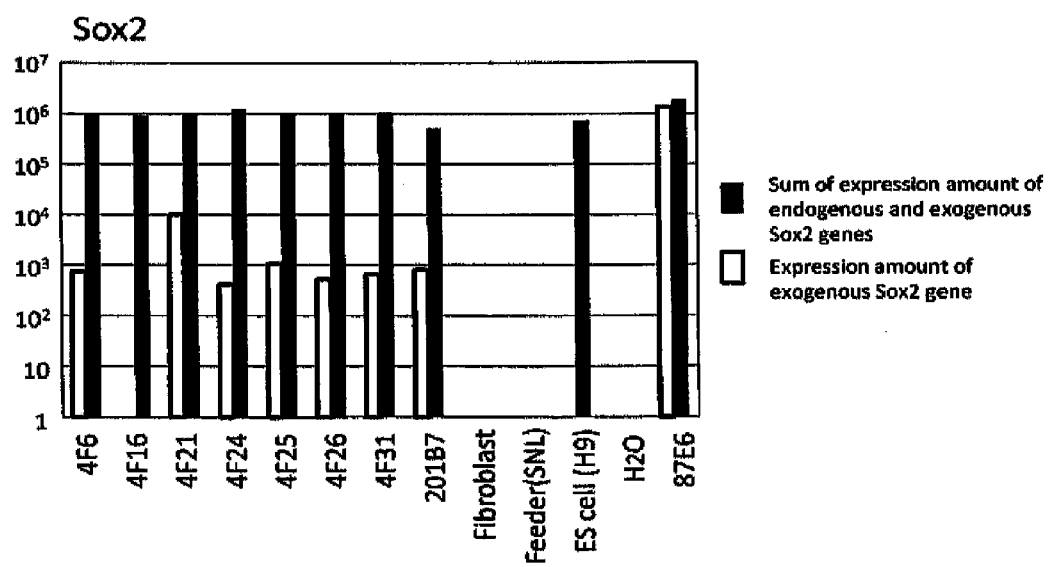
FIG. 2 shows the results of measurement of the expression level of the mRNA of Sox2.

In these graphs, the ordinate indicates the copy number of each transgene per 50 ng of the total RNA of the cells. Here, the copy number means the number of mRNAs. Each closed bar indicates the sum of the expression levels of an exogenous transgene and the corresponding endogenous gene in each type of cells, and each open bar indicates the expression level of an exogenous transgene.

Test iPS cells are represented as 4F2, 4F3, 4F4, 4F5, 4F6, 4F7, 4F8, 4F10, 4F12, 4F16, 4F19, 4F20, 4F21, 4F24, 4F25, 4F26 and 4F31, and 201B7 and 201B2 are the control iPS cell in which the expression of the exogenous genes is repressed. 87E6 is the control iPS cell in which the expression of the exogenous genes is not repressed.

DESCRIPTION OF THE PREFERRED EMBODIMENTS

The present invention provides a method for selecting an iPS cell in which expression of an exogenous transgene(s) (nuclear reprogramming gene(s)) used for establishment of the iPS cell is repressed.

I. Production Method of iPS Cells (A) Somatic Cell Source

Somatic cells which may be used as starting materials for preparation of iPS cells may be any cells other than germ cells derived from mammals (human, mouse, monkey, pig, rat and the like), and examples of the somatic cells include epithelial cells which are keratinized (e.g., keratinized epidermal cells), mucosal epithelial cells (e.g., epithelial cells of the lingual surface), epithelial cells of exocrine glands (e.g., mammary cells), hormone-secreting cells (e.g., adrenomedullary cells), cells for metabolism and storage (e.g., hepatic cells), luminal epithelial cells constituting boundary surfaces (e.g., type I alveolar cells), luminal epithelial cells in the closed circulatory system (e.g., vascular endothelial cells), ciliated cells having a carrying capacity (e.g., tracheal epithelial cells), extracellular matrix-secreting cells (e.g., fibroblasts), contractile cells (e.g., smooth muscle cells), cells involved in the blood system and the immune system (e.g., T lymphocytes), sensory cells (e.g., rod cells), autonomic neurons (e.g., cholinergic neurons), supporting cells of sense organs and peripheral neurons (e.g., satellite cells), nerve cells and glial cells in the central nervous system (e.g., astroglial cells) and pigment cells (e.g., retinal pigment epithelial cells), and progenitor cells (tissue progenitor cells) thereof. The level of differentiation of the cells and the age of the animal from which the cells are collected are not restricted, and either undifferentiated progenitor cells (including somatic stem cell) or terminally-differentiated mature cells may be used as sources of the somatic cells in the present invention. Here, examples of the undifferentiated progenitor cells include tissue stem cells (somatic stem cells) such as neural stem cells, hematopoietic stem cells, mesenchymal stem cells and dental pulp stem cells.

The mammal individual to be used as the source from which the somatic cells are collected is not restricted, and in cases where the obtained iPS cells are to be used for human regenerative medicine, it is preferred to collect somatic cells from the patient himself or another person having the same or substantially the same HLA type in view of prevention of the rejection reaction. Here, "substantially the same" HLA type means that the HLA type is matching to an extent which allows survival of the transplanted cells when the cells were obtained by differentiation induction from iPS cells derived from the somatic cells and then transplanted to the patient. For example, it means that another person has the same major HLAs (for example, the three loci including HLA-A, HLA-B and HLA-DR) as those of the patient. Also when the cells are not administered (transplanted) to human, for example, in cases where the iPS cells are used as sources of cells for evaluation of drug sensitivity of a patient or for evaluation of the risk of side effects, it is preferred to collect somatic cells from the patient himself or another person who has the same genotypes which are related to the drug sensitivity and the side effects.

The somatic cells separated from a mammal may be pre-cultured, before providing them for the nuclear reprogramming step, in a per se known culture medium suitable for culture of the cells, depending on the type of the cells. Examples of the culture medium include, but are not limited to, a minimum essential medium (MEM) supplemented with about 5 to 20% fetal bovine serum, Dulbecco's modified Eagle's medium (DMEM), RPMI1640 medium, 199 medium and F12 medium. When a gene transfer reagent such as cationic liposome is used upon contacting the cells with a nuclear reprogramming gene(s) (and, as required, another substance for improvement of the establishment efficiency of iPS cells), the culture medium may be preferably replaced with a serum-free medium to prevent decrease in the gene transfer efficiency.

(B) Transgene

The transgene used in the present invention means an exogenous gene having a nuclear reprogramming function (nuclear reprogramming gene), which is introduced in somatic cells in order to reprogram the nuclei of the somatic cells to establish iPS cells, and those described in WO 2007/069666 may be used. More particular examples thereof include Oct3/4, Klf4, Klf1, Klf2, Klf5, Sox2, Sox1, Sox3, Sox15, Sox17, Sox18, c-Myc, L-Myc, N-Myc, TERT, SV40 Large T antigen, HPV16 E6, HPV16 E7, Bmil, Lin28, Lin28b, Nanog, Esrrb and Esrrg. The transgene does not necessarily encode a protein, and may be an RNA described in *Science*, 296, 550-553 (2002) which has an RNA interference function against p53 and a DNA described in WO 2009/075119 which expresses a miRNA.

For establishment of iPS cells, a plurality of these transgenes may be used in an arbitrary combination. iPS cells may also be established by further inclusion of another arbitrary substance in the combination.

Preferred examples of the combination of the transgenes include, among the combinations above, the combination of 4 genes, that is, Oct3/4, Sox2, Klf4 and c-Myc.

The sequence information of the cDNAs of the above-described nuclear reprogramming factors in mouse and human can be obtained by reference to the NCBI accession numbers described in WO 2007/069666 (the sequence information of the cDNAs of Oct3/4, Sox2, Klf4, c-Myc, Lin28, Lin28b, Esrrb and Esrrg in mouse and human can be obtained by reference to the NCBI accession numbers below), and those skilled in the art can easily isolate these cDNAs.

| Gene name | Mouse | Human |
| --- | --- | --- |
| Oct3/4 | NM_013633 | NM_002701 |
| Sox2 | NM_011443 | NM_003106 |
| Klf4 | NM_010637 | NM_004235 |
| c-Myc | NM_010849 | NM_002467 |
| Lin28 | NM_145833 | NM_024674 |
| Lin28b | NM_001031772 | NM_001004317 |
| Esrrb | NM_011934 | NM_004452 |
| Esrrg | NM_011935 | NM_001438 |

When a nucleic acid encoding a protein is used as a nuclear reprogramming factor, the obtained cDNA is inserted into a virus vector, plasmid vector, episomal vector or the like to construct an expression vector, which is then used in the nuclear reprogramming step.

(C) Method of Gene Transfer to Somatic Cells

The cDNA of the nuclear reprogramming gene is inserted into an appropriate expression vector having a promoter which can function in a somatic cell which is used as the host. Examples of the expression vector which can be used include virus vectors such as retroviruses, lentiviruses and herpesviruses; and animal cell expression plasmids (e.g., pA1-11, pXT1, pRc/CMV, pRc/RSV and pcDNAI/Neo).

The type of the vector to be used may be appropriately selected depending on the use of the obtained iPS cells.

Examples of the promoter used in the expression vector include the EF1α promoter, CAG promoter, SRα promoter, SV40 promoter, LTR promoter, CMV (cytomegalovirus) promoter, RSV (Rous sarcoma virus) promoter, MoMuLV (Moloney murine leukemia virus) LTR and HSV-TK (herpes simplex virus thymidine kinase) promoter. Among these, the EF1α promoter, CAG promoter, MoMuLV LTR, CMV promoter, SRα promoter and the like are preferred.

The expression vector may comprise, as desired, in addition to the promoter, an enhancer, a poly (A) addition signal, a selection marker gene, a reporter gene, the SV40 replication origin and/or the like. Examples of the selection marker gene include the dihydrofolate reductase gene, neomycin resistance gene and puromycin resistance gene. Examples of the reporter gene include the genes encoding fluorescent proteins such as the green-fluorescent protein (GFP), yellow-fluorescent protein (YFP) and blue-fluorescent protein (BFP); luminescent proteins such as aequorin; and enzymes such as luciferase, β-galactosidase, alkaline phosphatase and horseradish peroxidase (HRP).

The transgenes may be separately incorporated in expression vectors, or 2 or more types, preferably 2 to 3 types of the genes may be incorporated in a single expression vector. Further, an expression vector to which 2 or more types of the genes are incorporated and an expression vector to which only one gene is incorporated may be used in combination.

Here, when a plurality of the transgenes (e.g., 2 or more selected from Oct3/4, Sox2, Klf4 and c-Myc: preferably 2 to 3 genes) are incorporated in a single expression vector, these plurality of genes may be incorporated into the expression vector preferably via a sequence(s) which enables polycistronic expression of the genes. By using the sequence(s) enabling the polycistronic expression, the plurality of genes incorporated in the single expression vector can be more efficiently expressed. Preferred examples of the sequence(s) which enable(s) the polycistronic expression include 2A sequences such as the 2A sequence in foot and mouth disease virus (SEQ ID NO: 2; PLoS ONE3, e2532, 2008; *Stem Cells* 25, 1707, 2007) and the IRES sequence (U.S. Pat. No. 4,937, 190 B). When a plurality of reprogramming genes are inserted into a single expression vector after being polycistronically linked to each other, the order of the reprogramming genes is not restricted, and, for example, these may be linked in the orders of (i) Sox2 and Klf4; and (ii) Oct3/4 and c-Myc; in the direction from 5' to 3'.

Vectors which express siRNAs are classified into the tandem type and the stem-loop (hairpin) type. In the former type, an expression cassette for the sense strand of a siRNA and an expression cassette for the antisense strand of the siRNA are tandemly linked, and a double-stranded siRNA (dsRNA) is formed by expression and annealing of the both strands in the cell. On the other hand, in the latter type, an expression cassette of a shRNA is inserted into a vector, and the shRNA is expressed in the cell and processed by Dicer to form a dsRNA. Examples of the promoter also include pol II promoters (e.g., the CMV immediate-early promoter), but a pol III promoter is commonly used for accurate transcription of a short RNA. Examples of the pol III promoter include the murine and human U6-snRNA promoters, the human H1-RNase P RNA promoter and the human valine-tRNA promoter. As a transcription termination signal, a sequence having not less than 4 consecutive "T"s may be used.

The expression vector containing the transgene(s) can be introduced to the cells by a per se known method depending on the type of the vector. For example, in the case of a virus vector, a plasmid containing the nucleic acid is introduced to an appropriate packaging cell line (e.g., Plat-E cells) or a complementing cell line (e.g., 293 cells), and the virus produced in the culture supernatant is recovered, followed by infection of the virus to cells by an appropriate method depending on the type of the virus vector. For example, particular methods using a retrovirus vector are disclosed in WO2007/69666; *Cell*, 126, 663-676 (2006); and *Cell*, 131, 861-872 (2007); and usage of a lentivirus vector is disclosed in *Science*, 318, 1917-1920 (2007).

On the other hand, when a nonviral plasmid vector is used, the vector can be introduced to the cells by using the lipofection method, liposome method, electroporation method, calcium phosphate coprecipitation method, DEAE-dextran method, microinjection method, gene gun method or the like. Particular examples of the method using a plasmid vector include those described in *Science*, 322, 949-953 (2008) and the like.

When a plasmid vector is used, the gene introduction may be carried out an arbitrary number of times which is not less than 1 (e.g., 1 to 10, 1 to 5, or the like). When two or more types of expression vectors are introduced to somatic cells, all of these types of vectors are preferably introduced to the somatic cells at the same time, and also in such cases, operation of the gene introduction may be carried out an arbitrary number of times which is not less than 1 (e.g., 1 to 10, 1 to 5, or the like). The operation of the gene introduction may be preferably repeated not less than twice (e.g., 3 or 4 times).

(D) Substances for Improvement of the Establishment Efficiency of iPS Cells

For establishment of the iPS cells, a substance for improvement of their establishment efficiency may be used, and examples of the substance include, but are not limited to, histone deacetylase (HDAC) inhibitors [e.g., low molecular inhibitors such as valproic acid (VPA) (*Nat. Biotechnol.*, 26(7): 795-797 (2008)), trichostatin A, sodium butyrate, MC 1293 and M344], G9a histone methyltransferase inhibitors [e.g., low molecular inhibitors such as BIX-01294 (*Cell Stem Cell*, 2: 525-528 (2008)], and L-calcium channel agonists [e.g., Bayk8644 (*Cell Stem Cell*, 3, 568-574 (2008)), UTF1 (*Cell Stem Cell*, 3, 475-479 (2008)), Wnt Signaling (e.g., soluble Wnt3a) (*Cell Stem Cell*, 3, 132-135 (2008)), and 2i/LIF (2i is an inhibitor of mitogen-activated protein kinase signalling and glycogen synthase kinase-3) (*PLoS Biology*, 6(10), 2237-2247 (2008))].

(E) Conditions for Establishment etc.

For establishment of iPS cells, the cells to which a nuclear reprogramming gene(s) has/have been introduced may be cultured, for example, under conditions suitable for culture of ES cells. In the case of murine cells, the culture is carried out in a normal culture medium supplemented with Leukemia Inhibitory Factor (LIF) as a differentiation inhibition factor. On the other hand, in the case of human cells, the culture medium is preferably supplemented with basic fibroblast growth factor (bFGF) and/or stem cell factor in place of LIF. Usually, the cells are cultured in the presence of fibroblasts as feeder cells derived from mouse embryos, which have been treated with radiation or antibiotics to stop their cell division. Usually, as the fibroblasts as the feeder cells derived from mouse embryos, the STO cell line (ATCC CRL-1503) or the like is commonly used, and, for induction of iPS cells, for example, SNL cells (SNL76/7 STO cells; ECACC 07032801) prepared by stable incorporation of the neomycin resistance gene and the LIF gene into STO cells (McMahon, A. P. & Bradley, A. Cell 62, 1073-1085 (1990)) are commonly used. However, in the present invention, since usage of primary fibroblasts derived from mouse embryos (MEFs) shows better improvement of the establishment efficiency of human iPS cells, MEFs are preferably used. Mitomycin C-treated MEFs are commercially available from MILLIPORE and Repro-CELL Inc. The coculture with such feeder cells may be started before, during, or after (e.g., 1 to 10 days after) the contact with the nuclear reprogramming factor(s).

The establishment efficiency of the iPS cells can be further improved by culturing the cells under hypoxic conditions during the nuclear reprogramming step. Here, the term "hypoxic condition" means that the oxygen concentration in the atmosphere during the culture of the cells is lower than that in the air. More particular examples of the condition include those where the oxygen concentration is lower than the oxygen concentration in the atmosphere of a 5 to 10% $CO_2$/95 to 90% air, and a condition where the oxygen concentration in the atmosphere is less than 18% is included in such examples. The oxygen concentration in the atmosphere is preferably less than 15% (e.g., less than 14%, less than 13%, less than 12% or less than 11%), less than 10% (e.g., less than 9%, less than 8%, less than 7% or less than 6%), or less than 5% (e.g., less than 4%, less than 3% or less than 2%). Further, the oxygen concentration in the atmosphere is preferably more than 0.1% (e.g., more than 0.2%, more than 0.3% or more than 0.4%), more than 0.5% (e.g., more than 0.6%, more than 0.7%, more than 0.8% or more than 0.95%), or not less than 1% (e.g., not less than 1.1%, not less than 1.2%, not less than 1.3% or more than 1.4%).

The method for creating a hypoxic state in the cellular environment is not restricted, and the simple and preferred examples thereof include a method wherein the cells are cultured in a $CO_2$ incubator with which the oxygen concentration can be controlled. The $CO_2$ incubator with which the oxygen concentration can be controlled is commercially available from various equipment manufacturers (for example, $CO_2$ incubators for hypoxic culture produced by manufacturers such as Thermo scientific, Ikemoto Scientific Technology Co., Ltd., Juji Field Inc. and Wakenyaku Co., Ltd. may be used).

The timing of initiation of the cell culture under hypoxic condition is not restricted as long as the establishment efficiency of iPS cells is improved as compared to the establishment efficiency in the case of a normal oxygen concentration (20%), and may be before, during, or after the contact with the nuclear reprogramming factor(s). For example, the culturing under hypoxic condition is preferably carried out immediately after the contact with the nuclear reprogramming factor(s), or a certain period (for example, 1 to 10 (2, 3, 4, 5, 6, 7, 8 or 9) days) after the contact with the nuclear reprogramming factor(s).

The length of time of the culture of cells under hypoxic condition is not restricted as long as the establishment efficiency of iPS cells is improved as compared to the establishment efficiency in the case of a normal oxygen concentration (20%), and examples of the length of time include, but are not limited to, not less than 3 days, not less than 5 days, not less than 7 days or not less than 10 days, and not more than 50 days, not more than 40 days, not more than 35 days or not more than 30 days. The preferred length of time of the culture under hypoxic condition varies depending on the oxygen concentration in the atmosphere, and those skilled in the art may appropriately control the culturing time depending on the oxygen concentration employed. Further, in one mode, when candidate colonies of iPS cells are selected using drug resistance as an index, the cells are preferably returned from the hypoxic condition to a condition where the oxygen concentration is normal.

Further, preferred timing of initiation of the cell culture under hypoxic condition and a preferred length of time of the culture vary depending on the type(s) of the nuclear reprogramming factor(s) employed and the establishment efficiency of iPS cells under a condition where the oxygen concentration is normal.

Examples of the method for selecting candidate colonies of iPS cells include methods using drug resistance and reporter activity as indices and methods by visual observation of morphology. Examples of the former method include those wherein the locus of a gene which is specifically and highly expressed in pluripotent cells (e.g., Fbx15, Nanog or Oct3/4; preferably Nanog or Oct3/4) is targeted by a drug resistance gene and/or a reporter gene to prepare recombinant somatic cells, which are used for selection of colonies which are positive for the drug resistance and/or the reporter activity. Examples of such recombinant cells include MEF derived from mouse wherein the βgeo gene (which encodes a fusion protein of β-galactosidase and neomycin phosphotransferase) has been knocked-in into the Fbx15 locus (Takahashi & Yamanaka, Cell, 126, 663-676 (2006)) and MEF derived from a transgenic mouse wherein the green-fluorescent protein (GFP) gene and the puromycin resistance gene have been incorporated into the Nanog locus (Okita et al., Nature, 448, 313-317 (2007)). On the other hand, examples of the method to select candidate colonies by visual observation of their morphology include the method described in Takahashi et al., Cell, 131, 861-872 (2007). Methods using reporter cells are simple and efficient, but, when iPS cells are prepared for the purpose of human therapy, visual selection of the colonies is preferred in view of safety.

The fact the cells of the selected colonies are iPS cells can be confirmed based on positivity of the Nanog (or Oct3/4) reporter (puromycin resistance, GFP positivity or the like) and visual observation of formation of ES cell-like colonies. Alternatively, tests such as alkaline phosphatase staining, analysis of expression of ES cell-specific genes, or confirmation of teratoma formation after transplantation of the selected cells to mice can also be carried out to obtain more accurate results.

II. Method for Measuring the Expression Level(s) of the Transgene(s)

A method to separately measure the expression level of the exogenous transgene(s) and sum of the expression levels of the exogenous transgene(s) and the corresponding endogenous gene in the thus established iPS cell will now be shown below. Here, the term "corresponding endogenous gene" means, for example, when the exogenous transgene is Oct3/4, the Oct3/4 gene which is endogenously expressed by the cell.

In terms of the expression level of the gene, a transcription product (hnRNA, mRNA, miRNA or the like) may be detected by the PCR method, LAMP method, Northern hybridization method, microarray method or the like, and, when the gene expresses a protein, the expression level may be measured by detecting a translation product (polypeptide, modified peptide or the like) by the RIA method, IRMA method, EIA method, ELISA method, LPIA method, CLIA method, immunoblotting or the like.

Here, preferably, when the expression level of the exogenous transgene is measured by using the PCR method, a sequence specific to the expression vector used for the gene introduction, which is not a sequence in the coding region of the endogenously expressed gene, is at least used for one of the primer set. Preferably, a sequence in the coding region of the endogenously expressed gene is used for one of the primer set. On the other hand, when sum of the expression levels of the exogenous transgenes and the corresponding endogenous genes is measured by using the PCR method, primers which are designed in two regions in the coding region of the gene and can amplify both exogenous and endogenous genes are used.

Examples of the primer set include those in Table 3 shown in Examples.

| Oct3/4: | exogenous + endogenous | primer set of SEQ ID NOs: 1 and 2 |
| | only exogenous | primer set of SEQ ID NOs: 9 and 10 |
| Sox2: | exogenous + endogenous | primer set of SEQ ID NOs: 3 and 4 |
| | only exogenous | primer set of SEQ ID NOs: 11 and 12 |
| Klf4: | exogenous + endogenous | primer set of SEQ ID NOs: 5 and 6, or primer set of SEQ ID NOs: 17 and 18 |
| | only exogenous | primer set of SEQ ID NOs: 13 and 14 |
| c-Myc: | exogenous + endogenous | primer set of SEQ ID NOs: 7 and 8, or primer set of SEQ ID NOs: 7 and 19 |
| | only exogenous | primer set of SEQ ID NOs: 15 and 16 |

Similarly, when the Northern hybridization method or the microarray method is used, a probe having a sequence specific to the expression vector, which is not contained endogenous transcript, is preferably employed for measuring exogenous gene and a probe having a sequence specific to a coding region is preferably employed for measuring sum of the exogenous and endogenous genes.

The thus measured expression level of the exogenous transgene, or the sum of the expression levels of the exogenous transgene and the corresponding endogenous gene, or the amounts of the transcription products as alternatives to the expression levels, are preferably represented with numerical values. For example, when PCR method is used, a method wherein ethidium bromide intercalated into the PCR product is visualized by UV irradiation and the expression level is represented with numerical values based on the intensity, and a method wherein the amount of the PCR product is represented with numerical values based on the fluorescence intensity of dyes such as SYBR Green. In addition, the amount of the PCR product can be represented with numerical values using real-time PCR, by a method well-known to those skilled in the art. Furthermore, when the Northern hybridization method is used, the expression level can be represented with numerical values by measuring the amount of the fluorescence or the radioisotope of the hybridized probe.

On the other hand, when the gene expresses a protein and the translation product of the exogenous transgene is measured, the expression level of the gene may be alternatively measured by, for example, measuring the expression level of a tag gene or a reporter gene expressed simultaneously with the exogenous gene. Examples of the tag gene include the GST tag, 6×His tag, c-Myc tag and HA tag. The expression levels of these tag genes can be measured using antibodies by a method well-known to those skilled in the art. Examples of the reporter gene include the above-mentioned fluorescent proteins such as the green-fluorescent protein (GFP), yellow-fluorescent protein (YFP) and blue-fluorescent protein (BFP); luminescent proteins such as aequorin; and luciferase, β-galactosidase, alkaline phosphatase and horseradish peroxidase (HRP). The expression levels of these reporter genes can be measured by measuring the fluorescence intensity, luminescence intensity, enzyme activity and the like by methods well-known to those skilled in the art.

Also when the above-described translation product is measured, the sum of the expression levels of an exogenous transgene and the corresponding endogenous gene may be measured by using an antibody which recognizes a part which is common between the exogenous gene and the endogenous gene, by a method well-known to those skilled in the art.

III. Method for Selecting iPS Cell in which Expression of a Transgene(s) is Repressed (A) Selection Method by Absolute Evaluation Since the numerical value corresponding to the expression level of the transgene is dependent on properties or abilities of the instrument and the like used for the measurement, the numerical value is preferably converted to a relative value with respect to a numerical value obtained by measurement using a standard solution. Examples of the standard solution to be employed include a standard solution in which the expression vector used for establishment of the iPS cell, whose molecular weight is known, is dissolved. For example, the number of the mRNAs (hereinafter referred to as copy number) contained in one cell may be used as an index of expression level. Other examples of the index of expression level include the copy number relative to a number proportional to the amount of cells such as the total amount of RNA or the total amount of DNA in the cell.

Upon selection of an iPS cell in which expression of the exogenous transgene is repressed, it is preferred to select an iPS cell in which the expression level is less than or equal to a control value which is a converted value in a control iPS cell wherein expression of the exogenous transgene is actually repressed. Here, Table 1 may be prepared by investigating the converted value of expression of the exogenous transgene in an available arbitrary iPS cell line in which the condition of expression of the exogenous transgene is known, and the control value may be a value which is preliminarily set such that the values of both the sensitivity and/or the specificity shown in Table 1 are not less than 0.9, not less than 0.95 or not less than 0.99. More preferably, the values of both the sensitivity and the specificity are 1. Here, when both the sensitivity and the specificity are 1, the control value is ideal since there is no false positive and no false negative at all. Examples of the available arbitrary iPS cell line include 201B1, 201B2, 201B3, 201B6 and 201B7 described in Takahashi et al., *Cell*, 131, 861-872 (2007).

TABLE 1

| | Number of iPS cells in which expression of exogenous transgene is repressed | Number of iPS cells in which expression of exogenous transgene is not repressed |
|---|---|---|
| Number of cells showing lower values than control value | A | C |
| Number of cells showing higher values than control value | B | D |
| | Sensitivity = A/(A + B) | Specificity = D/(C + D) |

Here, the control value for each transgene is preferably less than or equal to 10000, 5000, 1000, 900, 850, 840, 830, 820, 810 or 800 copies with respect to 50 ng of the cellular RNA. More preferably, the employed control value may be different among the transgenes, and in the case of Oct3/4 gene, the control value is preferably 18700, 853, 800, 700, 600, 500, 400 or 345 copies per 50 ng of the cellular RNA; in the case of Sox2 gene, the control value is preferably 7950, 5000, 1000, 900, 810 or 379 copies per 50 ng of the cellular RNA; in the case of Klf4 gene, the control value is preferably 2990, 1000, 685, 500, 400, 300, 200, 100, 50 or 23 copies per 50 ng of the cellular RNA; and in the case of c-Myc gene, the control value is preferably 4020, 1890, 500, 400, 300 or 270 copies per 50 ng of the cellular RNA. Upon the selection of an iPS cell, an iPS cell in which all the transgenes show the expression levels of less than or equal to the control value(s) may be selected, or an iPS cell in which only a part, three, two or one of the genes show(s) the expression level(s) of less than or equal to the control value(s) may be selected.

(B) Selection Method by Relative Evaluation

An iPS cell in which expression of an exogenous transgene is repressed can be selected by calculating the ratio of the expression level of the exogenous transgene relative to the sum of the expression levels of the exogenous transgene and the corresponding endogenous gene. For example, it is preferred to select an iPS cell in which the ratio is not more than the ratio in the control iPS cell wherein expression of the exogenous transgene is actually repressed (hereinafter referred to as the control ratio). Here, Table 2 may be prepared by investigating the expression of the exogenous transgene in an available arbitrary iPS cell line in which the condition of expression of the exogenous transgene is known, and the control ratio may be a value which is preliminarily set such that the values of both the sensitivity and/or the specificity shown in Table 2 are not less than 0.9, not less than 0.95 or not less than 0.99. More preferably, the values of both the sensitivity and the specificity are 1. Here, when both the sensitivity and the specificity are 1, the control ratio is ideal since there is no false positive and no false negative at all. Examples of the available arbitrary cell line include 201B1, 201B2, 201B3, 201B6 and 201B7 described in Takahashi et al., *Cell*, 131, 861-872 (2007).

TABLE 2

|  | Number of iPS cells in which expression of exogenous transgene is repressed | Number of iPS cells in which expression of exogenous transgene is not repressed |
|---|---|---|
| Number of cells showing lower values than control ratio | A | C |
| Number of cells showing higher values than control ratio | B | D |
|  | Sensitivity = A/(A + B) | Specificity = D/(C + D) |

Here, the preferred control ratio is 5%, 4%, 3%, 2%, 1.5%, 1.4%, 1.2%, 1.1% or 1% for any transgene. More preferably, the employed control ratio may be different among the transgenes, and in the case of Oct3/4 gene, the control ratio is 1.8%, 1.0%, 0.5%, 0.1%, 0.09%, 0.08%, 0.07%, 0.06% or 0.05%; in the case of Sox2 gene, the control ratio is 0.2%, 0.19%, 0.18%, 0.17% or 0.16%; in the case of Klf4 gene, the control ratio is 10.3%, 5%, 1.18%, 1%, 0.9%, 0.8%, 0.7%, 0.69%, 0.68% or 0.67%; and in the case of c-Myc gene, the control ratio is 5%, 4.7%, 4%, 3%, 2.7%, 2%, 1.5%, 1.4%, 1.2%, 1.1% or 1%. Upon the selection of an iPS cell, an iPS cell in which all the transgenes show the expression levels of less than or equal to the control ratio(s) may be selected, or an iPS cell in which only a part, three, two or one of the genes show(s) the expression level(s) of less than or equal to the control ratio(s) may be selected.

The present invention will be described in more detail by referring to Examples, but, the present invention is not restricted thereto.

EXAMPLES

Establishment of Human iPS Cells by a Retrovirus

Human iPS cells were established by the method described in Takahashi, K. et al. (*Cell*, 131: 861-872 (2007)). 201B7 and 201B2 cell lines established in the document were used. Using retroviruses which express human OCT3/4, human SOX2, human KLF4 and human c-MYC, test iPS cell lines were established from fibroblasts prepared from the skin of a patient suffering from Chronic Infantile Neurologic, Cutaneous, Articular syndrome (CINCA syndrome) with the consent of the patient. These test iPS cell lines were named 4F2, 4F3, 4F4, 4F5, 4F6, 4F7, 4F8, 4F10, 4F12, 4F16, 4F19, 4F20, 4F21, 4F24, 4F25, 4F26 and 4F31.

Measurement of the Expression Levels of the Genes and Selection of iPS Cells in which Exogenous Gene is Silenced.

Total RNA was extracted from each type of the iPS cells, and a 1 µg aliquot thereof was subjected to reverse transcription using the primer dT(20) and a reverse transcriptase Rever Tra Ace (TOYOBO), thereby reverse-transcribing mRNAs to complementary DNAs. The final volume of the reaction product was 20 µl. Using 1 µl of this reverse transcription product (corresponding to 50 ng of RNA) as a template and SYBR Green II as an index, quantitative PCR was carried out for each transgene using primer sets described in Table 3 for measurement of sum of the expression levels of the exogenous gene and the corresponding endogenous gene and for measurement of the expression level of the exogenous gene. The conditions for the amplification were as follows: 1 cycle of 95° C./30 seconds, followed by 50 cycles of (95° C./5 seconds, 60° C./30 seconds) for primer sets other than Klf4 (total)#2 in Table 3, or 50 cycles of (95° C./10 seconds, 60° C./10 seconds and, 72° C./40 seconds) for primer set of Klf4 (total)#2.

Subsequently, quantitative PCR was similarly carried out using as templates a solution containing $10^8$ molecules (hereinafter referred to as "copies")/µl of pMXs-human OCT3/4 (5833 base pairs, 1802397 g/mol), pMXs-human SOX2 (5560 base pairs, 1718040 g/mol), pMXs-human KLF4 (6020 base pairs, 1860180 g/mol) or pMXs-human c-Myc (5920 base pairs, 1829280 g/mol) which is a retrovirus vector used for the gene introduction and a 10-fold serial dilution thereof, to prepare calibration curves for the primer set of the each nuclear reprogramming genes for measurement of sum of the expression levels of the exogenous gene and the corresponding endogenous gene and the primer set for measurement of the expression level of the exogenous gene. Using these calibration curves, the results of the quantitative PCR for each type of the iPS cells were converted to the copy numbers with respect to 50 ng of the total RNA, for the sum of the expression levels of each exogenous gene and the corresponding endogenous gene, and for the expression level of the exogenous gene. In each of FIGS. 1 to 8, the ordinate indicates these copy numbers. The results from 4F6, 4F16, 4F21, 4F24, 4F25, 4F26, 4F31, 201B7, negative controls which are fibroblasts from which the iPS cells were derived, SNL cell used as a feeder cell, and embryonic stem cell (H9), and positive control which is 87E6 iPS cell line without silencing; are shown in FIGS. 1 to 4. In FIGS. 3 and 4, the primer set of Klf4(total)#1 and c-Myc(total)#1 were respectively used for measuring sum of the expression levels of Klf4 and c-Myc exogenous genes and the corresponding endogenous genes. In fibroblasts, SNL cell and H9 as negative control, no expression of the exogenous transgenes was observed, but expression of the endogenous genes was observed. The results from the 201B7 cell, which is a control iPS cell with silencing, are also shown in Table 4.

Figure 7:
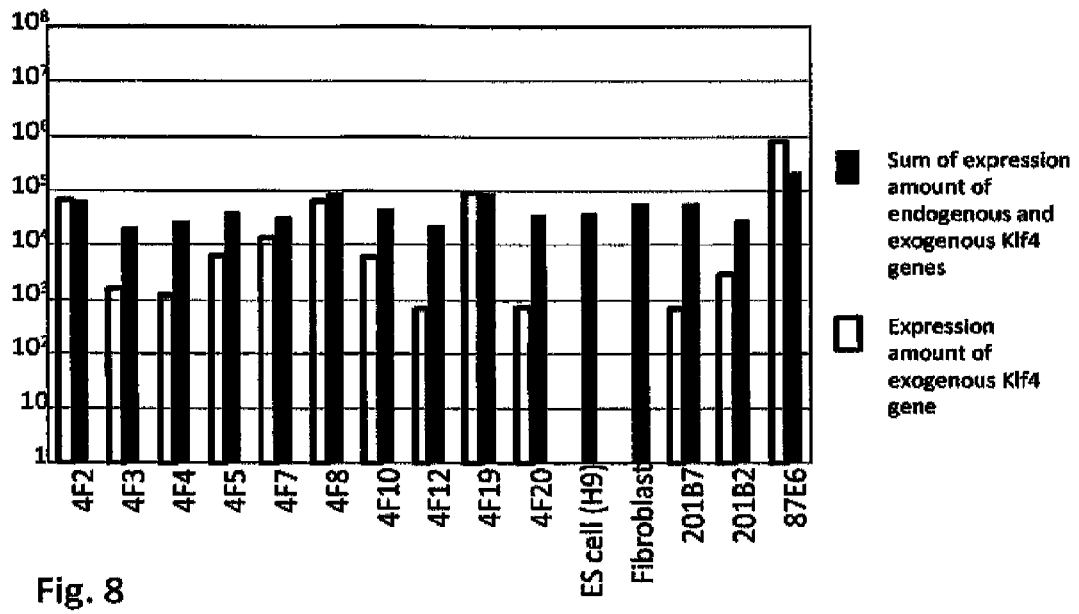
FIG. 7 shows the results of measurement of the expression level of the mRNA of Klf4.
Figure 8:
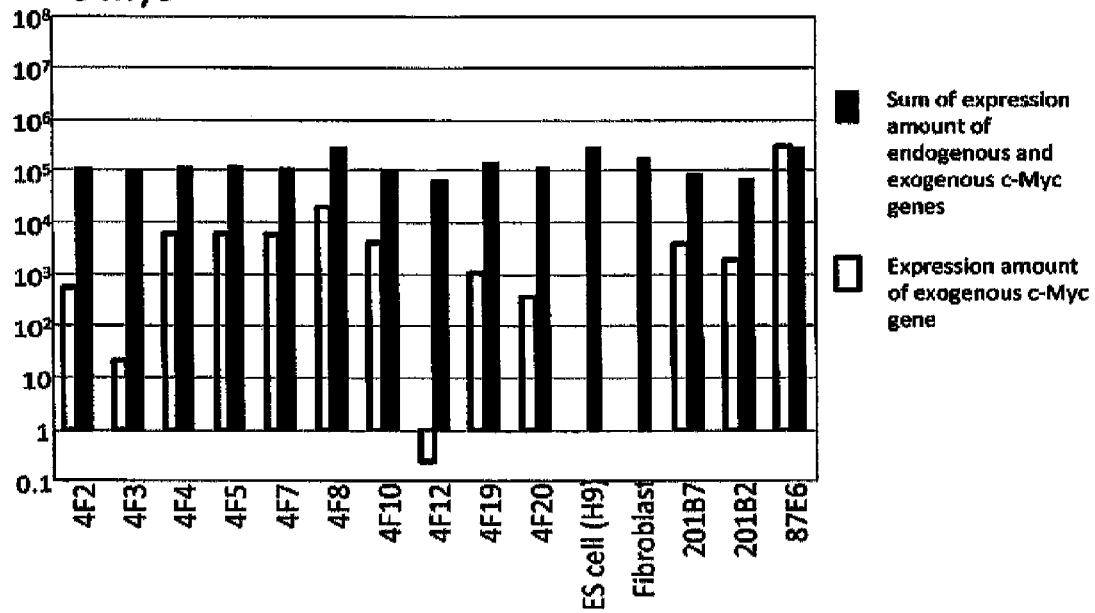
FIG. 8 shows the results of measurement of the expression level of the mRNA of c-Myc.

The results from 4F2, 4F3, 4F4, 4F5, 4F7, 4F8, 4F10, 4F12, 4F19, 4F20, 201B7, 201B2, negative controls, which are fibroblasts, SNL cell, and H9, and 87E6; are shown in FIGS. 5 to 8. In FIGS. 7 and 8, the primer set of Klf4(total)#2 and c-Myc(total)#2 were respectively used for measuring sum of the expression levels of Klf4 and c-Myc exogenous genes and the corresponding endogenous genes. The results from the 201B7 and 201B2 cell lines, which are control iPS cell lines with silencing, are also shown in Table 5 and 6.

From these results, test iPS cell lines in which expression of a transgene(s) is repressed were selected by comparison with the value of expression level of the exogenous gene of control iPS cell, and it was confirmed that exogenous genes were repressed in 4F3, 4F6, 4F12, 4F16 and 4F20 (Table 7). Additionally, when 10000 copies/50 ng of total RNA was used as control value, it was determined that exogenous genes were repressed in 4F3, 4F4, 4F5, 4F6, 4F10, 4F20, 4F24 and 4F26 (Table 7). In this case, the each "Sensitivity" for exogenous expression of Oct3/4, Sox2, Klf4, and c-Myc in Table 1 was respectively 88%, 100%, 100%, and 100%. Also, the each "Specificity" for exogenous expression of Oct3/4, Sox2, Klf4, and c-Myc in Table 1 was respectively 100%, 100%, 60%, and 14%.

TABLE 4

Results from 201B7 on the first try

| Transgene | Expression level of exogenous gene (copies/ 50 ng RNA) | Expression level of endogenous and exogenous genes (copies/50 ng RNA) | Ratio of expression level of exogenous gene relative to expression level of endogenous and exogenous genes (%) |
|---|---|---|---|
| Oct3/4 | 345 | 709000 | 0.048660085 |
| Sox2 | 810 | 514000 | 0.157587549 |
| Klf4 | 22.6 | 3390 | 0.666666667 |
| c-Myc | 270 | 25600 | 1.0546875 |

TABLE 5

Results from 201B7 on the second try

| Transgene | Expression level of exogenous gene (copies/ 50 ng RNA) | Expression level of endogenous and exogenous genes (copies/50 ng RNA) | Ratio of expression level of exogenous gene relative to expression level of endogenous and exogenous genes (%) |
|---|---|---|---|
| Oct3/4 | 853 | 3910000 | 0.021815857 |
| Sox2 | 7950 | 6310000 | 0.125990491 |
| Klf4 | 685 | 58300 | 1.174957118 |
| c-Myc | 4020 | 85900 | 4.679860303 |

TABLE 6

Results from 201B2

| Transgene | Expression level of exogenous gene (copies/ 50 ng RNA) | Expression level of endogenous and exogenous genes (copies/50 ng RNA) | Ratio of expression level of exogenous gene relative to expression level of endogenous and exogenous genes (%) |
|---|---|---|---|
| Oct3/4 | 18700 | 1030000 | 1.815533981 |
| Sox2 | 379 | 2350000 | 0.01612766 |
| Klf4 | 2990 | 28900 | 10.34602076 |
| c-Myc | 1890 | 70300 | 2.688477952 |

TABLE 3

Primer sets used for quantitative PCR

| Subject of measurement | | Sense strand Antisense strand | SEQ ID NO: |
|---|---|---|---|
| For measurement of sum of expression levels of the exogenous and endogenous genes | OCT3/4 (total) | ccccagggccccatttggtacc | 1 |
| | | acctcagtttgaatgcatgggagagc | 2 |
| | SOX2 (total) | ttcacatgtcccagcactaccaga | 3 |
| | | tcacatgtgtgagaggggcagtgtgc | 4 |
| | Klf4 (total)#1 | gattacgcgggctgcggcaaaacctacaca | 5 |
| | | ttaaaaatgtctcttcatgtgtaaggcgag | 6 |
| | Klf4 (total)#2 | catgccagaggagcccaagccaaagagggg | 17 |
| | | cgcaggtgtgccttgagatgggaactcttt | 18 |
| | c-Myc (total)#1 | atacatcctgtccgtccaagcaga | 7 |
| | | tcacgcacaagagttccgtagctgttcaag | 8 |
| | c-Myc (total)#2 | atacatcctgtccgtccaagcaga | 7 |
| | | acgcacaagagttccgtagctg | 19 |
| For measurement of expression level of the exogenous gene | OCT3/4 (transgene) | gctctcccatgcattcaaactga | 9 |
| | | cttacgcgaaatacgggcagaca | 10 |
| | SOX2 (transgene) | ttcacatgtcccagcactaccaga | 11 |
| | | gacatggcctgcccggttattatt | 12 |
| | Klf4 (transgene) | ccacctcgccttacacatgaaga | 13 |
| | | gacatggcctgcccggttattatt | 14 |
| | c-Myc (transgene) | atacatcctgtccgtccaagcaga | 15 |
| | | gacatggcctgcccggttattatt | 16 |

TABLE 7

| | Oct3/4 | | Sox2 | | Klf4 | | c-Myc | |
|---|---|---|---|---|---|---|---|---|
| | control iPS cell's value | defined value | control iPS cell's value | defined value | control iPS cell's value | defined value | control iPS cell's value | defined value |
| 4F2 | S | S | S | S | | | S | S |
| 4F3 | S | S | S | S | S | S | S | S |
| 4F4 | S | S | S | S | S | S | | S |
| 4F5 | S | S | S | S | | | S | S |
| 4F6 | S | S | S | S | S | S | S | S |
| 4F7 | S | S | | | | | | S |
| 4F8 | S | S | S | S | | | | |
| 4F10 | S | S | S | S | | S | S | S |
| 4F12 | S | | S | S | S | S | S | S |
| 4F16 | S | | S | S | S | S | S | S |
| 4F19 | S | S | S | S | S | S | | S |
| 4F20 | S | S | S | S | S | S | S | S |
| 4F21 | S | S | | | | | S | S |
| 4F24 | S | S | S | S | S | S | | S |
| 4F25 | S | S | S | S | | | S | S |
| 4F26 | S | S | S | S | | | S | S |
| 4F31 | S | S | S | S | | | | S |

"S" means silencing of exogenous gene determined by comparing control or defined value.
Control iPS cell value of Oct3/4 is 18700 copies/50 ng RNA
Control iPS cell value of Sox2 is 7950 copies/50 ng RNA
Control iPS cell value of Klf4 is 2990 copies/50 ng RNA
Control iPS cell value of c-Myc is 4020 copies/50 ng RNA
defined value is 10000 copies/50 ng RNA

The invention claimed is:

1. A method for selecting an induced pluripotent stem (iPS) cell line having increased safety for clinical application, said method comprising the steps of:

(a) obtaining an iPS cell line using exogenous nuclear reprogramming factors;

(b) measuring the expression level of all of the exogenous nuclear reprogramming factors in the iPS cell line;

(c) selecting an iPS cell line having increased safety for clinical application in which the expression level of each of the exogenous nuclear reprogramming factors is less than or equal to 10000 copies per 50 ng of total RNA in the iPS cell line.

2. The method according to claim 1, wherein said nuclear reprogramming factors are Oct3/4, Sox2, and Klf4.

3. The method according to claim 1, wherein said nuclear reprogramming factors are Oct3/4, Sox2, Klf4 and c-Myc.

4. The method of claim 1, wherein the expression level of each of the exogenous nuclear reprogramming factors is less than or equal to 1000 copies per 50 ng of total RNA in the iPS cell line.

5. The method according to claim 1, wherein the expression level of said exogenous nuclear reprogramming gene(s) is measured using a primer set comprising the nucleotide sequence of SEQ ID NO: 9 and 10, a primer set comprising the nucleotide sequence of SEQ ID NO: 11 and 12, and/or a primer set comprising the nucleotide sequence of SEQ ID NO: 13 and 14.

6. The method according to claim 1, wherein the expression level of said exogenous nuclear reprogramming genes is measured using a primer set comprising the nucleotide sequence of SEQ ID NO: 9 and 10, a primer set comprising the nucleotide sequence of SEQ ID NO: 11 and 12, a primer set comprising the nucleotide sequence of SEQ ID NO: 13 and 14 and/or a primer set comprising the nucleotide sequence of SEQ ID NO: 15 and 16.

* * * * *